(12) United States Patent
Huo et al.

(10) Patent No.: US 7,410,762 B1
(45) Date of Patent: Aug. 12, 2008

(54) METHOD FOR DETECTING BIOMOLECULES

(75) Inventors: Qisheng Huo, Albuquerque, NM (US); Jun Liu, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 235 days.

(21) Appl. No.: 11/168,247

(22) Filed: Jun. 27, 2005

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................... 435/6, 435/7.1; 536/23.1, 24.3
See application file for complete search history.

(56) References Cited

U.S. PATENT DOCUMENTS

| | | | |
|---|---|---|---|
| 6,051,380 A | 4/2000 | Sosnowski et al. | |
| 6,238,624 B1 | 5/2001 | Heller et al. | |
| 6,342,359 B1 * | 1/2002 | Lee et al. | 435/6 |
| 6,387,625 B1 | 5/2002 | Eckhardt et al. | |
| 6,484,046 B1 | 11/2002 | Say et al. | |
| 6,548,311 B1 | 4/2003 | Knoll | |
| 6,740,518 B1 * | 5/2004 | Duong et al. | 435/287.2 |
| 6,846,638 B2 | 1/2005 | Shipwash | |

OTHER PUBLICATIONS

Hyun C. Yoon, Biocatalitic precipitation induced by an affinity reaction on dendrimer-activated surfaces for the electrochemical signaling from immunosensors., The Analyst, 2002, 127, p. 1082-1087.
E. Palecek, DNA hydridization at microbeads with cathodic stripping voltammetric detection, Talanta 56 (2002) p. 919-930.
Joseph Wang, Indicator-free electrochemical DNA hybridization biosensor, Analytica Chimica Acta 375 (1998) p. 197-203.
Chunhai Fan, Electrochemical interrogation of conformational changes as a reagentless method for the sequence-specific detection of DNA, PNAS, vol. 100, No. 16, (Aug. 5, 2003) 9134-9137.
Christine Berggren, Capacitance Measurements of Antibody-Antigen Interactions in a Flow System, Anal. Chem. 1997, 69, 3651-3657.
Lievin Kumpumbu-Kalemba, Electrochemical characterization of monolayers of a biotinylated polythiophene: towards the development of polymeric biosensors, Chem. Commun., 2000, 1847-1848.

\* cited by examiner

*Primary Examiner*—Ethan Whisenant
(74) *Attorney, Agent, or Firm*—Elmer A. Klavetter

(57) ABSTRACT

A method for detecting and measuring the concentration of biomolecules in solution, utilizing a conducting electrode in contact with a solution containing target biomolecules, with a film with controllable pore size distribution characteristics applied to at least one surface of the conducting electrode. The film is functionalized with probe molecules that chemically interact with the target biomolecules at the film surface, blocking indicator molecules present in solution from diffusing from the solution to the electrode, thereby changing the electrochemical response of the electrode.

18 Claims, 6 Drawing Sheets

METHOD FOR DETECTING BIOMOLECULES

This invention was made with Government support under Contract No. DE-AC04-94AL85000 awarded by the Department of Energy. The Government has certain rights in the invention.

BACKGROUND OF THE INVENTION

The invention describes a method for detecting biomolecules and, more particularly, to a method using an electrochemical sensor device for detecting biomolecules based on self-assembled nanoporous films on conducting electrodes.

Electrochemical methods are useful in the detection and analysis of biomolecules because they can be simple, fast, sensitive, reliable and inexpensive. These methods are particularly suitable for reduction-oxidation (redox) active proteins and enzymes. However, many biomolecules are not redox active and do not produce an electrochemically detectable signal. Therefore, most electrochemical assays require the target to be labeled with a redox active agent (markers or indicators) or an enzyme.

There has been an increasing interest in sensitive, labeling-free electrochemical detection for biomolecules. Enzyme catalyzed precipitation on an electrode has been investigated for detection for biomolecules. The diffusion of ferrocene markers in the bound layer for avidin-biotin coupling has also been studied. Other researchers have studied various redox complexes that were sensitive to their chemical environments for use in biochemical detection. Recently, functionalized conjugated conductive polymers as the electrodes have shown encouraging results. Impedance and capacitance measurement were also investigated for direct measurement.

Besides proteins, electrochemical methods are widely studied for deoxyribonucleic acid (DNA) analysis. Most methods are based hybridization with labeled target biomolecules. Recently, a reagentless method for sequence-specific DNA detection was developed. This method depends on the conformation change of a beacon molecule—a DNA molecule composed of a hairpin-like DNA-loop structure upon hybridization. Other labeling free analysis includes methods to measure a change in intrinsic redox properties, catalytic reactions with a redox mediator, formation of electroactive oxidized product on the electrode, and stripping of detectable subunits.

BRIEF DESCRIPTIONS OF THE DRAWINGS

FIG. 4 shows cyclic voltammetry and differential pulse voltammetry curves over six orders of magnitude of concentration.

DESCRIPTION OF SPECIFIC EMBODIMENTS

The present invention comprises a method for utilizing a simple, robust and general platform for sensitive and labeling-free biomolecular detection. In one embodiment of the method of the present invention, nanoporous films of controlled porosity, generally self-assembled nanoporous films, are applied to a conducting electrode to form a sensor platform with at least one surface of the nanoporous film in contact with a solution containing the target biomolecules to be detected. The conducting electrode can comprise a conducting substrate or a non-conducting substrate, such as a glass, plastic or ceramic, coated with a conducting film. The nanoporous film must have a very uniform pore dimension and be capable of being functionalized at the surface, functioning as a "nanogate device". The functionalization of the surface of the film of the sensor platform allows chemical reaction or interaction of the target biomolecules with the sensor platform, with the target biomolecules essentially captured on the film's pore surfaces. When the target biomolecules are captured on the pore surfaces through specific binding or hybridization, the nanopores are totally or partially blocked. As a result, the diffusion of indicator molecules in the solution in pore channels is affected and the redox current measured across the electrode is changed. This method is effective in measuring the presence of fempto-mole target biomolecules.

Figure 1:
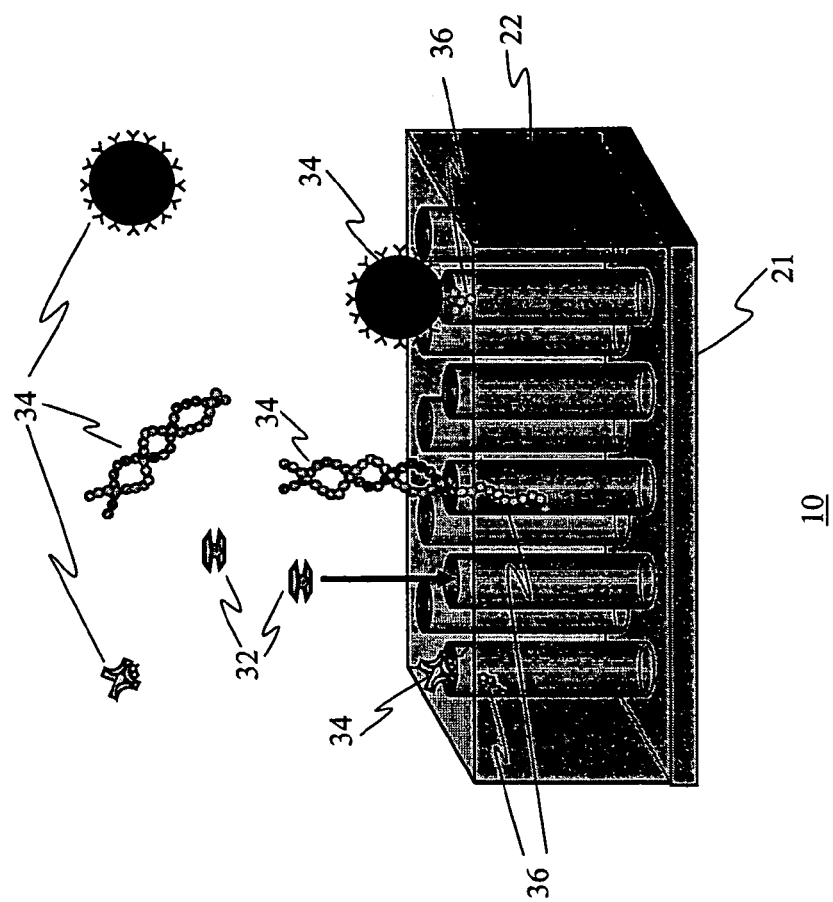
FIG. 1 shows an illustration of one embodiment of the sensor device

The key component of any molecular detection device is a capability to detect and quantify a wide variety of biomolecules. The detection principle embodied in the device of the present invention enables the device to be used as a general sensing platform because the concept is based on the electrochemical properties of the electrode resulting from the interaction (e.g., binding or hybridization) between probe molecules (immobilized on the self-assembled nanoporous film on the conducting electrode surface) and target biomolecules (from solution), which results in partial or complete blocking of the pore channels. FIG. 1 is a schematic illustration of one embodiment of the sensor device. The device 10 is in contact with a solution containing target biomolecules 34 (any of a variety of molecules, including, but not limited to, proteins, DNA, or other complex biomolecules) and, generally, indicator molecules 32. There is generally only one type of target biomolecule in solution but multiple types can be present. The nanopore surfaces of the nanoporous film 22 deposited on the electrode 21 can be functionalized with a wide variety of molecules 36 (that is, the probe molecules), including a biotin, an oligonucleotide, an antibody, or other molecules that serve to functionalize the surface for subsequent interaction with a target biomolecule. When specific binding occurs, the diffusion of the indicator molecules 32 in the pore channels is affected, resulting in a change, including up to complete, of the redox signal measured on the electrode 21. The electrode 21 is electrically connected to a measurement means (not shown) to determine the change in electrochemical response and subsequently determine the concentration of the target biomolecules.

For the device to function advantageously, the electrode and film material should meet several requirements. The pore size of the film material must be capable of being controlled so that the pore size is comparable with the dimension of the biomolecules. If the pore size is too large, pore blocking will not occur. On the other hand, leakage can be a problem if the biomolecules are much larger than the pore dimension. The pore dimension also significantly affects the kinetics of the diffusion of the indicator molecules. Large indicator molecules tend to diffuse slowly in the pore channels and distort the electrochemical signals.

Additionally, the pore sizes should be uniform. Non-uniform size distribution will cause some pores to be blocked and other pore to be open, making the device unworkable. Also, the nanoporous film should be defect free. A single defect (a crack, or a large open pore) will cause the whole device to fail. In the context of the present invention, defect free means that any cracks or large pores with the largest dimension greater than 30 nm comprise less than 1% of the total area of the surface. Finally, the nanoporous film should have flexible surface chemistry for functionalization. The materials should be stable, inexpensive and easy to fabricate into thin coatings on conductive substrates.

Self-assembled nanoporous films are materials that can satisfy these requirements. This type of nanoporous materials is prepared using a self-assembled, surfactant micellar structure as the template. They have extremely uniform pore sizes as compared to traditional sol-gel materials, and the pore size can be adjusted over a wide range (from 1.5 nm to 30 nm, with the mean diameter divided by the variance generally less than about 4). In addition, methods to functionalize the pore have been extensively investigated. Spin coating, dip coating, and other standard film coating techniques can be used to apply the films to a wide range of substrate materials.

The self-assembled, nanoporous films comprise a precursor sol, where the precursor sol is an aqueous solution generally prepared from a surfactant, a solvent, and a compound selected from tetra-alkoxysilanes, an alkoxysilane, such as tetraethylorthosilicate or tetramethylorthosilicate, or a metal alkoxide, including titanium butoxide, titanium iso-propoxide, zirconium n-butoxide, aluminum iso-propoxide, aluminum iso-propoxide, and mixtures thereof.

In one embodiment, a homogeneous solution of an alkoxysilane $Si(OR)_4$, a polar solvent, water, an organoalkoxysilane as the interstitial compound and a surfactant is prepared, wherein importantly the initial surfactant concentration, c, is less than the critical micelle concentration, cmc. Any organoalkoxysilane compound can be used but certain compounds are useful for their specific functionality. For example, organoalkoxysilanes with fluorinated groups, such as tridecafluoro-1,1,2,2,-tetrahydrooctyltriethoxysilane (TFTS), make the film hydrophobic and compounds with mercapto-terminated groups, such as mercaptopropyltrimethoxylsilane, can absorb heavy metals.

The surfactant can be anionic, cationic, nonionic, or a block copolymer. Anionic surfactants that can be used include, but are not limited to, sulfates, sulfonates, phosphates, and carboxylic acids. Cationic surfactants that can be used include, but are not limited to, alkylammonium salts, gemini surfactants, cetylethylpiperidinium salts, and dialkyldimethylammonium. Nonionic surfactants that can be used, with the hydrophilic group not charged, include, but are not limited to, primary amines, poly(oxyethylene) oxides, octaethylene glycol monodecyl ether and octaethylene glycol monohexadecyl ether. One useful block copolymer is a non-ionic surfactant, poly(ethylene oxide)-block-poly(propylene oxide)-block-poly(ethylene oxide) triblock copolymer (referred to hereinafter as $EO_xPO_yEO_z$, of which one useful block copolymer is $EO_{106}PO_{70}EO_{106}$; other variations with different contents of ethylene oxide and propylene oxide can be used. The polar organic/water solvent can be any general polar organic solvent soluble in water, such as an alcohol/water solvent, a formamide/water solvent or a tetrahydrofuran/water solvent.

Solvent evaporation induces micellization, or aggregation of micelles, and therefore continuous self-assembly of the surfactants and silicates into hybrid silica-surfactant mesophases. When the solvent evaporation is accomplished by spin-coating, spray-coating or dip-coating, a porous thin film is formed on a substrate which yields, after surfactant removal, a thin film with a narrow pore size distribution, typically from approximately 1 nm to approximately 20 nm, and a relatively high surface area, typically greater than 100 $cm^2/cm^2$ (film). and frequently greater than 500 $cm^2/cm^2$ (film). Particles can be formed by using aerosol processing or spray drying. Using organoalkoxysilane molecules, the organic ligands are covalently bonded to the framework and positioned on the pore surfaces in the present invention to achieve desired functionality. After the self-assembly process, the surfactant templates can be removed while preserving the organo-silicon bonds. This can be accomplished by using a low-temperature heat treatment or washing procedure. Extraction with ethanol is a very good method to remove surfactant templates from the film in the method of this invention and does not collapse the mesoporous network. Low temperature pyrolysis is another method to remove surfactant in the film. Alternatively, the hybrid silica-surfactant mesophase can be treated with a catalyst to promote the framework polymerization prior to surfactant removal.

In another preparation to form thin films on a substrate, a silica sol was prepared from tetraethylorthosilicate (TEOS), a polar organic solvent, water and an acid with addition of an organoalkoxysilane, for example, tridecafluoro-1,1,2,2,-tetrahydrooctyltriethoxysilane (TFTS), and a surfactant, such as cetyltrimethylammonium bromide (CTAB). The polar organic solvent can be any solvent that solubilizes the other reactants, particularly such solvents as alcohols, and more particularly, methanol, ethanol, propanol, butanol, tetrahydrofuran, and formamide or mixtures thereof. In a typical preparation, an initial silica sol was prepared by refluxing tetraethylorthosilicate (TEOS), ethanol, water and an acid, such as HCl, with addition of TFTS and CTAB. A thin film was prepared from this solution by spray-coating, dip-coating, or spin-coating on a substrate. During the coating procedure, evaporation of the solvent causes organization into the mesophase structure. Subsequently, the films were pyrolyzed in an oxygen or inert environment at elevated temperature to form an ordered mesoporous structure. These films were shown to be useful in sensor applications as films of thickness less than 1 micron had pore sizes between approximately 1 nm and approximately 10 nm, with a surface area greater than 500 $cm^2/cm^2$ (film).

Modifications of this preparation allow both ordered and disordered thin films to be prepared. Ordered films, more crystalline in characteristics, as determined by low angle x-ray diffraction, and disordered films, more amorphous in characteristics, are useful in different applications. As typical with the thin films prepared according to the present invention, both the ordered and disordered thin films have a relatively monodisperse pore size distribution. The ordered thin films have a two-dimensional and even three-dimensional regularity, as shown by transmission electron microscopy.

In another embodiment, the non-ionic surfactant $EO_{106}PO_{70}EO_{106}$ was used as the surfactant template to prepare the nanoporous film. A conductive film was coated with a nanoporous organic-inorganic hybrid silica thin film with covalently bonded, positively chargeable —$NH_2$ terminal groups by dip coating the electrode substrate from a solution containing tetraethoxysilicate (TEOS), 3-aminopropyltriethoxysilicate (APTS), and the nonionic surfactant ($EO_{106}PO_{70}EO_{106}$) under acid conditions. In a typical preparation, 0.5 g of HCl (1 mole/liter) was added into 5.45 g $EO_{106}PO_{70}EO_{106}$/ethanol (EtOH) solution (5 wt. %). Then a mixture containing 1.0 g TEOS and 0.095 g APTS was added with stirring. The sol was aged at room temperature for 1 hour. Indium Tin Oxide (ITO) substrates (ITO coated glass slides from Delta Technologies, or ITO coated polyester film OC50 from CPFilms) were coated with the nanoporous film by dip coating from the as prepared solution. Other conducting electrode materials could also be used, as known in the art. After the films were dried at room temperature for 1 day or longer, they were placed in a Soxhlet extractor using ethanol as the extraction solvent for 1 day to remove the surfactant. The electrodes modified with the nanoporous films were dried in air.

The $EO_{106}PO_{70}EO_{106}$ surfactant used produces large pore sizes that are desired for the sensing applications of interested. The nanofilm structure was characterized with transmission electron microscopy and showed that the film has a continuous, disordered and uniform pore structure. The mean pore diameter is approximately 8 nm with a variance of less than 2 nm. Depending upon the application, either an ordered pore geometry or a disordered pore geometry might be more effective. Rather the continuous nature of the disordered film will help ensure the connectivity of the pore channels though out the film and to the conductive surface.

Figure 2:
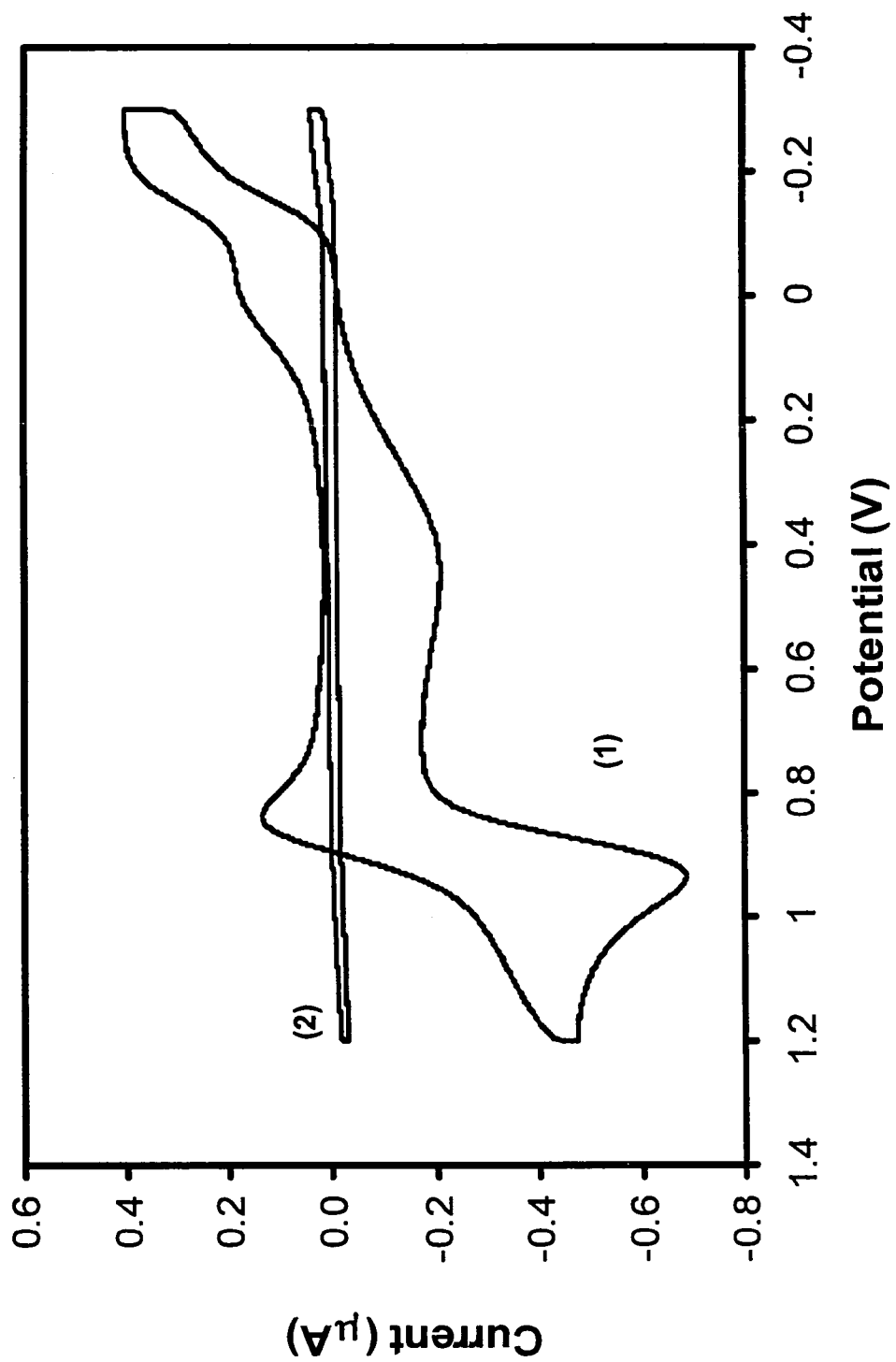
FIG. 2 shows the cyclic voltammetry curves of the biotinylated device in the absence and presence of streptavidin with different indicators.

In one embodiment to investigate the biosensor system of the present invention, biotin/streptavidin coupling was used as a model reaction. Streptavidin is made of four identical units (M. W. 60000) and has a strong affinity for biotin with a high binding constant of $10^{-15}$ $M^{-1}$ (corresponding to a binding energy of 20 kcal/mol). Many biotinylated molecules and avidin conjugates are commercially available, making this coupling one of the mostly widely studied reactions for biosensing. When enough target biomolecules are captured for complete coverage of all the reaction surface, almost all nanopores are blocked. In this case, the conductive layer (indium tin oxide, ITO in our experiments) of the electrode is isolated from the indicator molecules in electrochemistry testing solution and no redox response is detected. FIG. 2 shows the cyclic voltammetry (CV) curves of the biotinylated nanogate device in the absence and presence of $8.3 \times 10^{-10}$ mole (0.83 nmole) streptavidin with several indicators, $Fe(phen)_3^{3+}$, $Co(phen)_3^{2+}$, (where phen is an abbreviation for phenanthroline) and $Ru(NH_3)_6^{3+}$ in aqueous solution. An indicator molecule is a molecule in solution that, upon contacting the conducting electrode an electrochemical response (such as a current change) occurs. Without the streptavidin, multiple redox peaks are observed, as shown in curve (1). The peaks at 0.94V, 0.43V, and −0.08V corresponding to anodic potentials of $Fe(phen)_3^{3+}$, $Co(phen)_3^{2+}$, and $Ru(NH_3)_6^{3+}$ respectively. After streptavidin binds to biotin, the pores are completely blocked, and the CV curve is almost compressed to the horizontal line, as shown in curve (2). These results also indicate that the nanoporous film was continuous and pin-hole free, and that the fictionalization with biotin, and the biotin-streptavidin coupling is effectively demonstrating the pore blocking sensing mechanism. A kinetics study found that it took one to 3 hours for the pore blocking to occur. Blocking is faster for large indicator molecules and slow for small indicator molecules.

A detailed study of the CV curves and differential pulse voltammetry (DPV) curves at different streptavidin concentrations suggested three regions. DPV curves are helpful because the background contributions are removed. Absolute mole is used as the concentration unit as the absolute amount is more relevant to total surface coverage on the electrode. All CV and DPV measurements were performed with a CH Instruments Model 660A electrochemical analyzer (CH Instruments Inc., Cordova, Tenn., USA). The working electrode sensing area was 4-10 $mm^2$. The electrodes were immersed in appropriate electrolyte solutions containing indicator molecules. The voltammetric parameters used, unless stated otherwise, were (a) CV, scan rate 0.05 V/s and (b) DPV, pulse amplitude 0.02 V, pulse width 0.05 s. All electrochemical experiments were carried out in a conventional three-electrode cell containing an Ag/AgCl/KCl 3 M reference electrode and a platinum foil counter electrode. The supporting electrolyte is a 0.1 mole·$l^{-1}$ potassium phosphate buffer (pH=7.5) solution containing 0.15 mole·$l^{-1}$ potassium nitrate unless specified otherwise.

Figure 3:
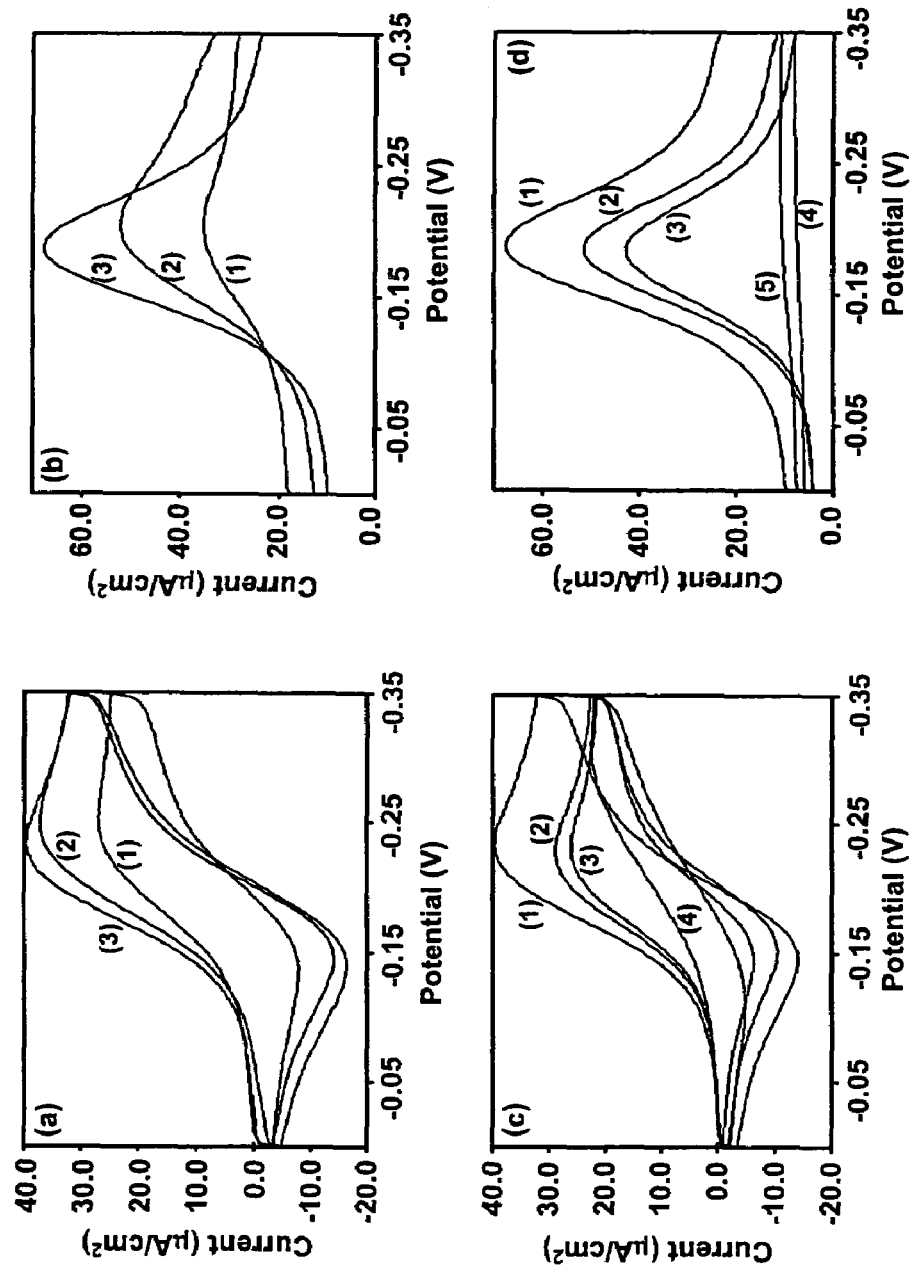
FIG. 3 shows the redox current as a function of streptavidin concentration.

At very low concentrations of the streptavidin molecules (below 13 fmole streptavidin), the redox current increases with concentration (FIGS. 3a and 3b, where in both figures curve (1) is for a streptavidin concentration of 0.13 fmole, curve (2) is for a concentration of 1.3 fmole, and curve (3) is for a concentration of 13 fmole). At this concentration, the number of streptavidin molecules is not enough to cause significant pore blocking. However, at the testing pH conditions, the streptavidin molecules are negatively charged and the indicator molecules ($Ru(NH_3)_6^{3+}$) are positively charged. Increasing biding of negatively charged streptavidin on the electrode surfaces increases the Coulomb attraction for the oppositely charged indicator molecules. The net effect is an increased number of indicator molecules on the electrode, which results in the increasing electrochemical response.

At a higher concentration of streptavidin molecules (13 fmole), the nanopores become partially blocked and the diffusion of the indicator molecules is impacted. The redox current decreases with streptavidin concentration in this region (FIGS. 3c and 3d). In FIG. 3c, curve (1) is for a streptavidin concentration of 13 fmole, curve (2) is for a concentration of 130 fmole, curve (3) is for a concentration of 1.3 pmole, and curve (4) is for a concentration of 1.3 nmole. In FIG. 3d, curve (1) is for a streptavidin concentration of 13 fmole, curve (2) is for a concentration of 130 fmole, curve (3) is for a concentration of 1.3 pmole, curve (4) is for a concentration of 13 pmole, and curve (5) is for a concentration of 1.3 nmole. At even a higher streptavidin concentration (13 pmole), the pores are completely blocked and no significant redox peaks are observed. The number of molecules required to completely block the pore surface were approximated, assuming an active electrode area about 40 $mm^2$, assuming that each streptavidin molecule occupies an area of approximately 30 $nm^2$ (according to molecular size 5.4×5.8×4.8 nm), and assuming that it takes one monolayer of molecules to cover the electrode surface and block the redox activity. It was determined that approximately $2 \times 10^{-12}$ mole (or approximately 2 pmole) of streptavidin are needed to block the pores. Experimentally, effective blocking is observed between 1.3 pmole and 13 pmole, which is close to the approximation.

Figure 4:
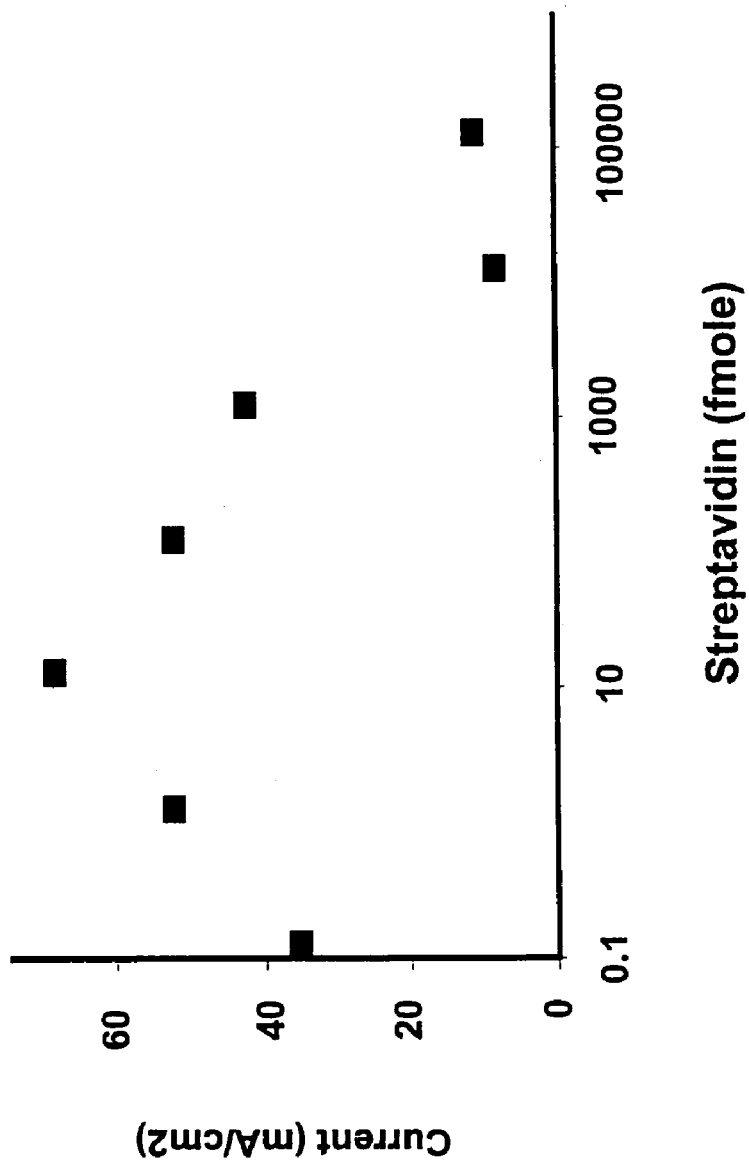
FIG. 4 shows current densities from differential DPV curves at various streptavidin concentrations

The redox current densities from the differential DPV curves are plotted in the FIG. 4. The current increases initially due to the Coulomb attraction between streptavidin and the indicator molecules, and then decreases due to pore blocking. From this figure, the change in the CV curve is detected at below fmole level (0.13 fmole). The more interesting pore blocking phenomena are observed at about 13 fmole level. Total pore blocking is observed at 13 pmole level. The results indicate that the self-assembled nanogate sensors have the capability of fmole level sensitivity, which is attractive for such simple bulk devices.

Figure 5:
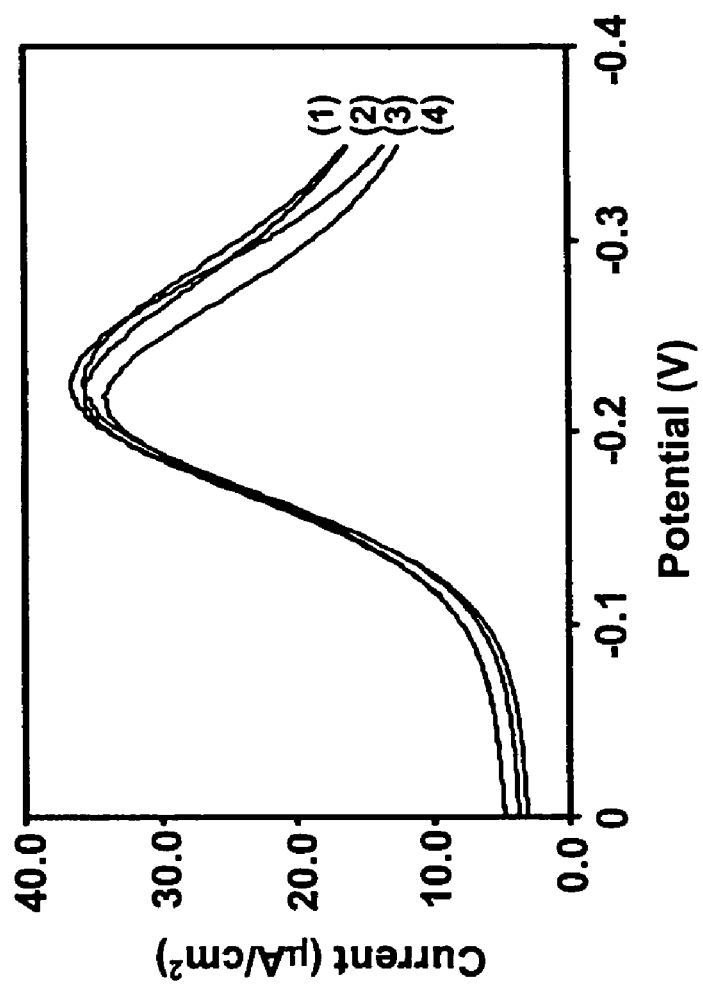
FIG. 5 shows the differential pulse voltammetry curves in the detection of DNA hybridization on a DNA functionalized nanoporous film-coated electrode.

To test the selectivity of the nanogate sensors, a control experiment on electrodes coated with nanoporous films without the biotin functionalization was carried out. These electrodes were reacted with strepavidin over a wide range of streptavidin concentrations under the same conditions as those for biotin functionalized electrodes. The CV and DPV curves are all similar from sub fmole to 1.2 nmole, over six orders of magnitudes (FIG. 5, where curve (1) is for a streptavidin concentration of 1.2 nmole, curve (2) is for a concentration of 0.1 nmole, curve (3) is for a concentration of 12 pmole, and curve (4) is for a concentration of 1.2 pmole). No concentration dependence is observed in these controlled experiments. These results suggest that the main mechanism of absorption and pore block is specific to the biotin-streptavidin. Non specific absorption plays insignificant role.

Figure 6:
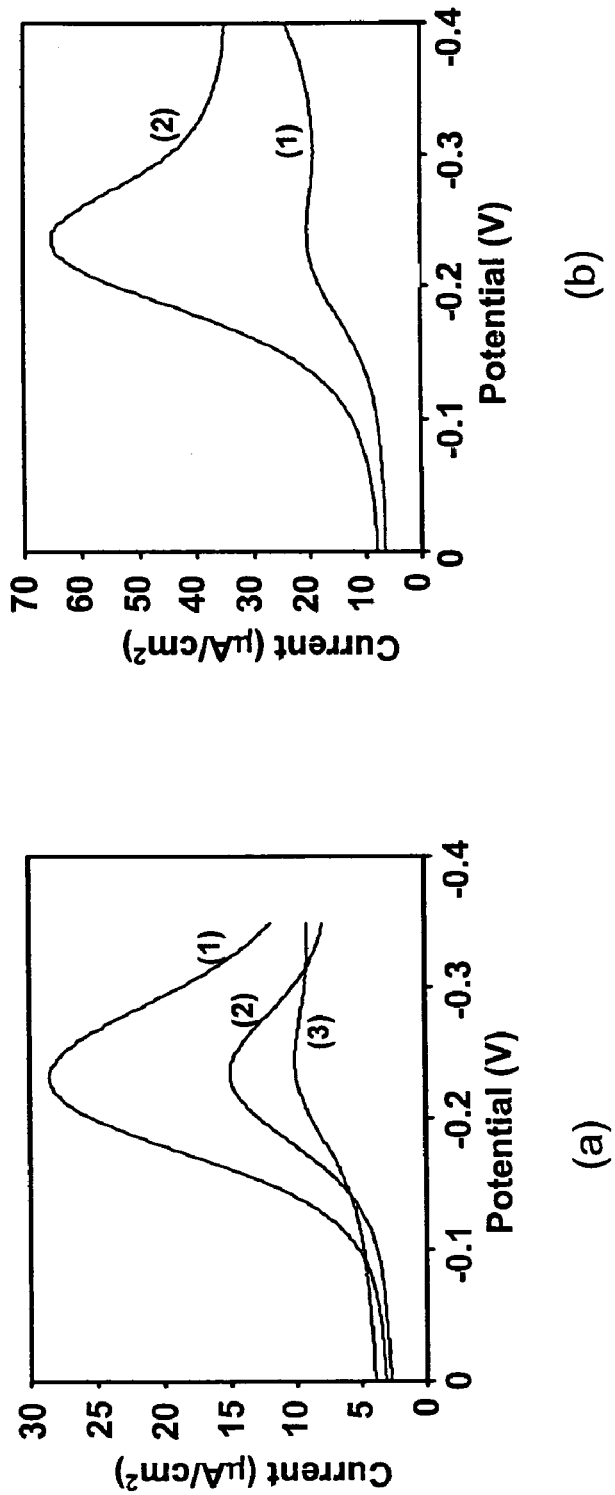
FIG. 6 shows the differential pulse voltammetry curves in the detection of DNA hybridization on a DNA functionalized nanoporous film-coated electrode.

The nanogate mechanism is universal and can be used for a wide range of biomolecules. Detection of DNA hybridization on DNA functionalized nanoporous film coated ITO electrode was tested. FIG. 6 shows the DPV scans in 0.5 mM $Ru(NH_3)_6^{3+}$ in 0.1 M potassium phosphate buffer solution (with 0.1 M $KNO_3$) (pH=7.5). Clear electrochemical peaks corresponding to the redox reaction of $Ru(NH_3)_6^{3+}$ for CV and DPV measurements are observed in the absence of target DNA molecules in the solution. The redox current exhibits a large decrease upon the hybridization of a target (complementary) DNA sequence, depending on the target concentration in the solution. More targeted molecules in the solution caused a larger reduction in the current density (FIG. 6a, where curve 91) is for a complementary DNA concentration of 1 pmole, curve (2) is for a concentration of 10 pmole and curve (3) is for a concentration of 10 nmole). The pore blocking behavior of complementary and non-complementary DNA segments (FIG. 6b, where curve (1) is for complementary DNA binding and curve (2) is for non-complementary DNA binding) was also investigated, finding that the complementary DNA causes a large reduction of the redox current due to pore blocking, while the non-complementary DNA did not cause significant pore blocking.

Complete pore blocking for DNA binding was not observed with the small indicator molecules ($Ru(NH_3)_6^{3+}$ in this case), but was observed for large indicator molecules (tris(1,10-phenanthroline) Fe(II), or $Fe(phen)3^{2+}$). The linear configuration of DNA molecules makes complete pore blocking difficult, but this problem does not affect how this methods can be used because it mainly depends on measuring the change (reduction) of the redox current.

The simple and robust sensor device based on self-assembled nanoporous electrodes for labeling-free biomolecular detection serves as a nanogate device having many advantages. It is a general platform for biosensors because the nanogate concept can be applied to different specific biomolecular coupling. This method does not require the biomolecules to have specific electrochemical activities. The sample preparation and electrochemical testing procedures are simple, straightforward and fast, with good sensitivity and selectivity.

In another embodiment of the method of the present invention, no indicator molecules are required in the solution that contacts the sensor platform. There exists a potential difference that is measured between the conducting electrode and the solution itself. Nanoporous films, generally self-assembled nanoporous films, are applied to a conducting electrode to form a sensor platform with at least one surface of the nanoporous film in contact with a solution containing the target biomolecules to be detected. The conducting electrode can comprise a conducting substrate or a non-conducting substrate, such as a glass, plastic or ceramic, coated with a conducting film. The nanoporous film does not require a uniform pore dimension but must be capable of being functionalized at the surface. The functionalization of the surface of the film of the sensor platform allows chemical reaction or interaction of the target biomolecules with the sensor platform, with the target biomolecules essentially captured on the film's pore surfaces. When the target biomolecules are captured on the pore surfaces through specific binding or hybridization, the potential difference between the solution and the conducting electrode changes, indicating the presence of the target biomolecules in solution or indicating a change in concentration of the target biomolecules in solution.

EXAMPLES

Example 1

Immobilization of Biotin onto Mesoporous Film and Biotin Streptavidin Coupling Reactions 0.25 g of d-biotin was dissolved in a mixture of 4.5 g of N,N-dimethyl formamide (DMF) and 0.5 g of water. 0.38 g diisopropylethylamine (DIEA) and 0.39 g N,N,N',N'-tetramethyl (succinimido) uronium tetrafluoroborate (TSTU) were added to this solution, and reacted for 15 minutes to form hydroxysuccinimide. The nanoporous film coated electrode was inserted to this solution and the solution was shaken at room temperature overnight. The hydroxylsuccinimide ester bound to the amine groups in the film. Finally the film was washed with water.

LC-biotin contains a long anchoring chain and reacts more readily with streptavidin. To functionalize the nanoporous film with LC-biotin, 10 mg biotinamidohexanoic acid N-hydroxysuccinimide ester (NHS-LC-biotin from) was dissolved in a solution containing 0.48 g of DMF and 0.12 g diisopropylethylamine. The nanoporous film was covered with this solution (0.02 g of solution per 10 $mm^2$ nanoporous film) at room temperature for overnight. The film was washed with water.

After the nanoporous film was functionalized with biotin, 0.9 g of solution containing different amount of streptavidin in phosphate buffer (pH about 7.5) was placed over the nanoporous film (approximately 40 $mm^2$ reaction area) and reacted for different time periods. The sample was washed with water at the end of the reaction.

Example 2

Immobilization of Oligonucleotide and Hybridization

To activate the surface for oligonucleotide immobilization, the nanoporous film was placed in 3.0 g acetonitrile, followed by the addition of 0.16 g diisopropylethylamine (DIEA). After brief shaking, 0.1 g cyanuric chloride was added and the reaction mixture was shaken for 4 hours at room temperature. The film was washed three times with acetonitrile and twice with sodium borate buffer (pH 8.5).

5'-(C6-Amino)TTT GAA MG GGA CGT GCG CTT CGA A-3' (probe) (SEQ. ID. 1), 5'-TTC GAA GCG CAC GTC CCT TTT CAA-3' (target) (SEQ. ID. 2), and 5'-CAG TCA GTC AGT CAG TCA GTC AGT-3' (non-target) (SEQ. ID. 3), were obtained from the Midland Certified Reagent Company, TX. The activated nanoporous film was covered with 0.03 g solution (1 mole·$l^{-1}$ sodium chloride, 0.05 mole·$l^{-1}$ sodium borate buffer, pH 8.5) containing 4 nmole probe molecules, and reacted overnight at room temperature. The sample was washed with water at the end of reaction.

Hybridization of complementary oligo (target) to the film containing immobilized probes was carried out as follow: the functionalized nanoporous film was covered with 30 mg of solution of target oligonucleotide in a hybridization buffer (0.1 mole·l⁻¹ potassium phosphate, 1 mole·l⁻¹ sodium chloride, 0.1% Tween-20, and 5% ethanol, pH 7.6). The film was washed with hybridization buffer to remove excess target oligonucleotides after the reaction. The control experiments (treatment with non-target oligonucleotide) were carried out under the same condition.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

measuring current across said conducting electrode to detect the presence of said target biomolecules.

2. The method of claim 1 where wherein said self-assembled film has a controllable pore size distribution with pores having diameters in the range of 1.5 nm to 30 nm.

3. The method of claim 2 wherein said pore size distribution has a value of the mean pore diameter divided by the variance of less than 4.

4. The method of claim 1 wherein said film is defect-free.

5. The method of claim 1 wherein the conducting electrode comprises a conducting substrate material.

6. The method of claim 1 wherein the conducting electrode comprises an indium tin oxide material.

We claim:

1. A method for detecting biomolecules, comprising: contacting a solution containing target biomolecules and indicator molecules with a sensor platform, said sensor platform comprising a nanoporous film deposited on a conducting electrode, said nanoporous film functionalized with probe molecules that chemically interact with said target biomolecules, wherein said nanoporous film is a self-assembled film, said self-assembled film comprising a precursor sol, said precursor sol comprising an aqueous solution prepared from a surfactant, a solvent, and a compound selected from tetraalkoxysilanes, an alkoxysilane, and a metal alkoxide, and 7. The method of claim 1 wherein the conducting electrode comprises a non-conducting substrate material coated with a conducting film.

8. The method of claim 7 wherein the non-conducting substrate material is selected from a plastic, a glass, and a ceramic.

9. The method of claim 1 wherein said indicator compound is selected from iron phenanthroline, cobalt phenanthroline and ruthenium phenanthroline.

10. The method of claim 1 wherein said plurality of target biomolecules comprises a material selected from a protein and DNA.

11. The method of claim 1 wherein said surfactant is selected from an anionic surfactant, a cationic surfactant, a nonionic surfactant, and a block copolymer surfactant.

12. The method of claim 1 wherein said surfactant is a poly(ethylene oxide)-block-poly(propylene oxide)-block-poly(ethylene oxide) triblock copolymer of the general formula $EO_xPO_yEO_z$.

13. The method of claim 12 wherein said surfactant is $EO_{106}PO_{70}EO_{106}$.

14. The method of claim 1 wherein said film is a self-assembled film, said self-assembled film comprising a precursor sol, said precursor sol comprising an aqueous solution prepared from $EO_{106}PO_{70}EO_{106}$, tetraethoxysilicate, and 3-aminopropyltriethoxysilicate under acidic conditions.

15. The method of claim 1 wherein said probe molecules comprise biotin and the target biomolecules comprise streptavidin.

16. The method of claim 1 wherein said target biomolecules comprise DNA molecules.

17. The method of claim 1 wherein said plurality of target biomolecules comprise a concentration of less than 10 nmoles in solution.

18. A method for detecting biomolecules, comprising:

contacting a solution containing target biomolecules with a sensor platform, said sensor platform comprising a nanoporous film deposited on a conducting electrode, said nanoporous film functionalized with probe molecules that chemically interact with said target biomolecules, and measuring the potential difference between said solution and said conducting electrode to detect said target biomolecules.

* * * * *

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: oligonucleotide modified with 5'-Amino Modifier
      six six-carbon compound (i.e., NH2-CH2-CH2-CH2-CH2-CH2-CH2-)
      that acts as a linker between oligonucleotide and
      nanoporous silica surface.

<400> SEQUENCE: 1
tttgaaaagg gacgtgcgct tcgaa                                          25

<210> SEQ ID NO 2
<211> LENGTH: 24
<212> TYPE: DNA
<213> ORGANISM: Artificial Sequence
<220> FEATURE:
<223> OTHER INFORMATION: target oligonucleotide that can hybrid with the
      probe oligonucleotide.

<400> SEQUENCE: 2
ttcgaagcgc acgtcccttt tcaa                                           24

<210> SEQ ID NO 3
<211> LENGTH: 24
<212> TYPE: DNA
<213> ORGANISM: Artificial Sequence
<220> FEATURE:
<223> OTHER INFORMATION: Synthetic DNA, non-target oligonucleotide that
      cannot hybrid with the probe oligonucleotide

<400> SEQUENCE: 3
cagtcagtca gtcagtcagt cagt                                           24
```